United States Patent [19]

Kim

[11] Patent Number: 4,643,161
[45] Date of Patent: Feb. 17, 1987

[54] METHOD OF MACHINING HARD AND BRITTLE MATERIAL

[76] Inventor: George A. Kim, 4754 N. Jenny Rd., Indianapolis, Ind. 46208

[21] Appl. No.: 773,590

[22] Filed: Sep. 9, 1985

Related U.S. Application Data

[62] Division of Ser. No. 628,024, Jul. 5, 1984, Pat. No. 4,581,969.

[51] Int. Cl.⁴ ............................................. B28D 5/00
[52] U.S. Cl. .................................. 125/30 R; 51/283 R; 51/229; 125/39
[58] Field of Search ................. 51/229, 122, 283 R; 125/30 R, 39

[56] References Cited

U.S. PATENT DOCUMENTS

| | | | |
|---|---|---|---|
| 1,955,128 | 4/1934 | Henderson | 51/263 |
| 2,858,730 | 11/1958 | Hanson | 88/14 |
| 3,043,060 | 7/1962 | Bell | 51/122 |
| 3,060,781 | 10/1962 | Villalobos | 83/651 |
| 3,190,047 | 6/1965 | Villalobos | 51/283 |
| 3,447,366 | 6/1969 | Villalobos | 73/104 |
| 3,646,841 | 3/1972 | Villalobos | 83/171 |
| 3,834,265 | 9/1974 | Tafapolsky et al. | 83/651 |
| 3,877,705 | 4/1975 | Joschko et al. | 274/38 |
| 4,084,942 | 4/1978 | Villalobos | 51/307 |
| 4,104,832 | 8/1978 | Keizer | 51/281 |
| 4,164,680 | 8/1979 | Villalobos | 313/336 |
| 4,181,505 | 1/1980 | De Vries et al. | 51/307 |
| 4,269,092 | 5/1981 | Disharoon | 83/42 |
| 4,273,561 | 6/1981 | Villalobos | 51/307 |
| 4,319,889 | 3/1982 | Villalobos | 51/307 |
| 4,328,646 | 5/1982 | Kaganowicz | 51/281 |
| 4,340,954 | 7/1982 | Chio et al. | 369/173 |
| 4,428,165 | 1/1984 | Dholakia | 51/283 R |

Primary Examiner—Harold D. Whitehead
Attorney, Agent, or Firm—Barnes & Thornburg

[57] ABSTRACT

An ultramicrotome diamond tool is provided with a diamond knife blade having first and second planar surfaces which intersect to define a cutting edge and a shank for holding the knife blade. In one embodiment of the ultramicrotome diamond tool the cutting edge of the blade is defined by the intersection of naturally occurring (111) and (100) crystal planes and is primarily usable in materials science and machine tool applications. In a second embodiment of the ultramicrotome diamond tool, the cutting edge of the blade is defined by the intersection of naturally occurring (320) and (111) crystal planes and is primarily usable in biological science applications to cut biological tissue or the like. The blade is usable to cut a material specimen that has a longitudinal axis and that is being advanced in a direction along its longitudinal axis toward the ultramicrotome tool. The blade is mounted on a shank having a longitudinal axis. The shank is mounted on a base to cause the longitudinal axis of the shank to be substantially orthogonal to the longitudinal axis of the material specimen.

27 Claims, 12 Drawing Figures

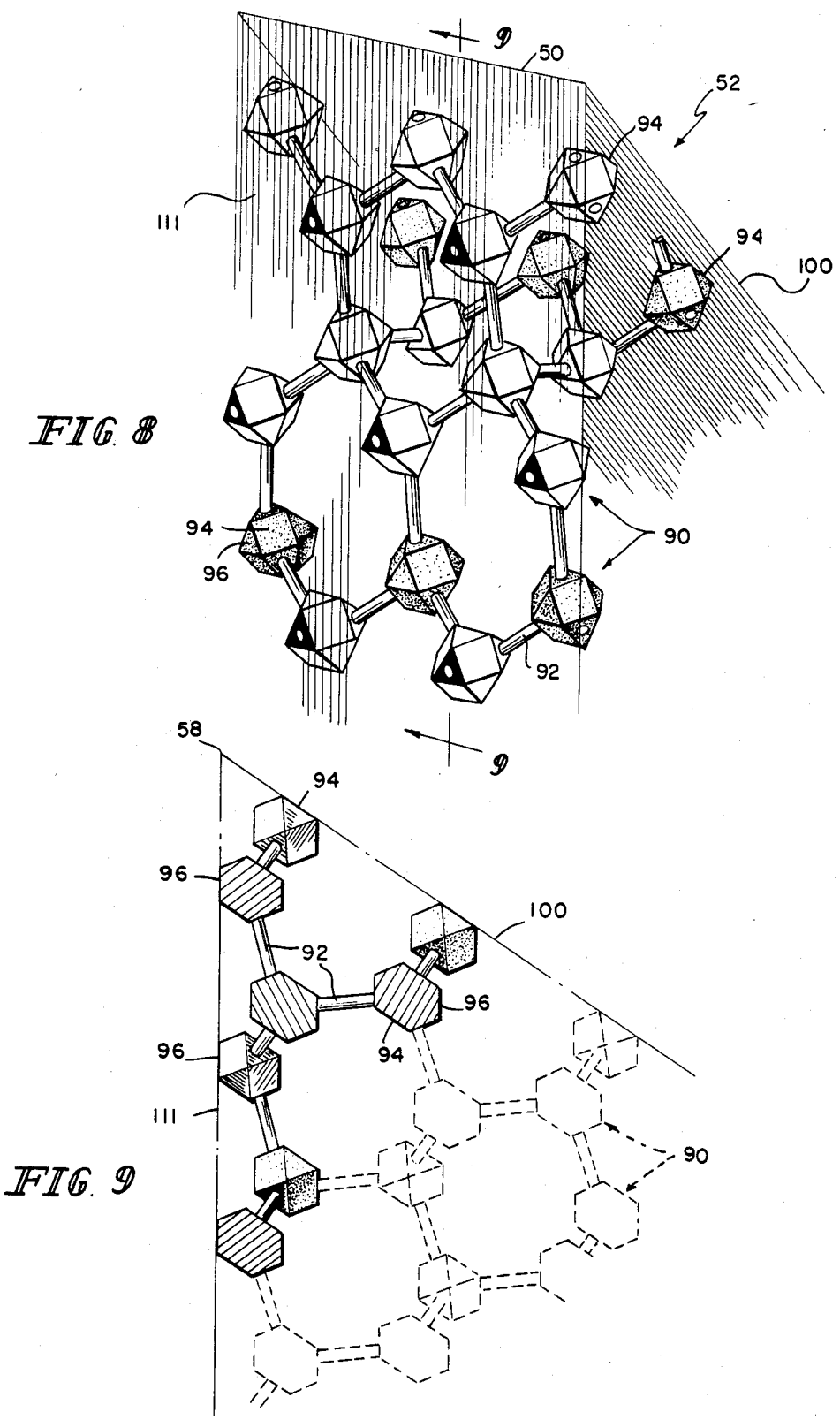

METHOD OF MACHINING HARD AND BRITTLE MATERIAL

This is a division of application Ser. No. 628,024, filed July 5, 1984, now U.S. Pat. No. 4,581,969.

This ivention relates to ultramicrotome diamond tools and particularly to a diamond tool blade having a cutting edge at the intersection of two naturally occurring crystal planes within the diamond structure of the blade.

Ultramicrotome diamond tools are used to slice very thin sections from a material specimen such as biological tissue to provide a thin specimen for study under a scanning or transmission electron microscope. These tools are also used in the materials science art to cut plastics, metals, or the like.

The chief problem encountered during the operation of a conventional ultramicrotome diamond tool or knife is "chatter". Chatter is the rapid vibration of the knife blade with respect to the material specimen causing the knife blade to cut the specimen unevenly. A material specimen is freguently irreparably damaged or spoiled if it has been sliced by a chattering knife blade. One cause of chatter is an unsharp or easily dulled knife blade cutting edge. A less than sharp knife blade will bind as it cuts through the material specimen to produce an unclean, wavy cut. Another cause of chatter is exposure of the knife blade to an external vibration. For example, a shop floor may transmit vibrations caused by a seismic wave or by operation of a forklift truck or the like to cause a conventional ultramicrotome diamond knife blade to vibrate in an unwanted manner while a material specimen is being cut. Such an unwanted vibration deleteriously affects the plane of the cut by unpredictably changing the position of the cutting edge relative to the material specimen. Destruction of a non-replaceable material specimen or repetition of a time-consuming cutting operation are two disadvantageous effects of knife blade chatter.

One type of conventional ultramicrotome diamond knife is illustrated in FIGS. 1 and 2. FIG. 1 shows an idealized cubic-type diamond crystal 10 with eight exposed octahedral faces 12. Each octahedral face 12 is coincident with a naturally occurring (111) crystal plane of the diamond crystal 10. This style of diamond crystal is typically used as a base from which all types of diamond tools are constructed. A diamond platelet 14 is manually cleaved from the diamond crystal 10 by an experienced gem cutter. The platelet 14 is cleaved along a (111) crystal plane (defined by broken lines in FIG. 1) parallel to the outwardly presented octahedral face 14.

Two steps are required to transform the platelet 14 into a diamond knife blade 16 of the type shown in FIG. 2. First, the triangle-shaped platelet 14 is "squared-up" to form a rectangular parallelepiped (not shown) having mutually parallel (111) crystal planar faces 18 and 20. Second, the "squared up" platelet 14 is machined to include facets 22 and 24. A conventional cutting edge 26 is defined by the intersection of facets 22 and 24. Typically, facets 22 and 24 cooperate to define a dihedral included angle of about 40° to 50° therebetween. The conventional blade 16 shown in FIG. 2 is easily identified by its characteristic cross-sectional "roof-top" shape.

In the past, diamond platelets such as platelet 14 were never machined or polished directly on a naturally occurring crystal plane such as the (111) plane because it was difficult to identify the location of those planes and not economical to do so once such a plane was identified. Instead, gem cutters machined the platelet 14 six or seven degrees off of the (111) plane as shown in FIG. 2 and obtained the characteristic "roof-top" shape. Typically, the diamond platelet is fully cut and prepared before it is mounted on a shank. It is difficult to consistently identify and cut along a crystal plane within acceptable tolerances using such a standard technique.

Experienced gem cutters are able to identify a (111) "three-point" crystal plane and a (100) "four-point" crystal plane by their characteristic symmetry. However, many other crystal planes such as a (320) plane are not so easily identified. Identification of such planes would permit exploitation of many combinations of cutting-edge defining planes not known in the prior art. One object of the present invention is to identify and machine diamonds on crystallographic planes to obtain a sharper and stronger cutting edge that is less susceptible to "chatter".

The conventional diamond knife blade 16 is mounted in a metal shank 28 to provide a conventional diamond knife assembly 30. The knife assembly 30 is usable to slice a material specimen 32. Typically, a conventional material specimen 32 is movable in directions 34 and 36 in relation to fixed knife assembly 30. Specimen 32 is indexable in direction 34 to lie in proximity to cutting edge 26 and reciprocable in direction 36 to contact cutting edge 26 such that a very thin section 38 of the material specimen 32 is sliced with each downward stroke of the specimen 32. The fixed knife assembly 30 is oriented such that its longitudinal axis 40 is rotated at an angle 42 of about 20° to 30° with respect to the vertical 44. Canting of the shank 28 to maintain such an orientation is a contributing cause of chatter. This typical orientation further causes facet 22 to be orthogonal to the axial direction 34 along which the material specimen 32 is incrementally indexed.

Conventional ultramicrotome diamond tools do not perform well under normal operating conditions due to loss of cutting edge sharpness and due to the susceptability of conventional blade holding shanks to external vibration. According to the present invention, an improved ultramicrotome diamond tool including a blade faceted substantially along naturally-occurring crystal planes to create a sharper and stronger cutting edge and including vertically upright blade holding shank to better resist the influence of external vibrations minimizes "chatter" and advantageously avoids the shortcomings of conventional ultramicrotome diamond knives.

In accordance with the present invention, an ultramicrotome diamond tool or knife includes a knife blade having first and second naturally occurring planar surfaces which intersect to define a cutting edge and a shank for holding the knife blade. The blade is made by first cutting a (111) plane and then cutting along a second naturally occurring crystal plane at an acute angle in relation to the (111) plane. Thus, a blade of the present invention has a characteristic "wedge" shape and not the "roof-top" shape of conventional diamond knife blades.

The present invention advantageously reduces the unwanted effects of knife blade chatter by causing the cutting edge of the diamond tool to be substantially at the intersection of two naturally occurring crystal planes of a diamond or other similar cubic crystalline structure. It will be understood that both natural and artificially manufactured gems or crystals have naturally occurring crystal planes.

According to one illustrative embodiment, the first planar surface is substantially coplanar with a (111) crystal plane and the second planar surface is substantially coplanar with a (100) crystal plane. The first and second planar surfaces intersect to define a dihedral angle of about 54.7°. This first embodiment of the ultramicrotome tool is primarily usable in materials science and machine tool applications to cut a material such as copper or ceramic. The knife blade is brazed into a milled cutout in the shank so that the (111) crystal plane presents a forwardly-facing vertically upright blade surface and the (100) crystal plane presents a upwardly-facing blade surface. Thus, the sharper and stronger cutting edge of the blade in the first embodiment of the ultramicrotome diamond tool is defined by the intersection of naturally occurring (111) and (100) crystal plane.

According to another illustrative embodiment of the present invention, the first planar surface is substantially coplanar with a (320) crystal plane and a second planar surface is substantially coplanar with a (111) crystal plane. The first and second planar surfaces intersect to define a dihedral angle of about 36.8°. In contrast to the first embodiment, the second embodiment of the ultramicrotome tool is primarily usable in biological science applications to cut biological tissue or the like. The blade is brazed into an end milled slot in the shank so that the (320) crystal plane presents a forwardly-facing, vertically upright blade surface and the (111) crystal plane presents an upwardly-facing blade surface. Thus, the sharper and stronger cutting edge of the blade in the second embodiment of the ultramicrotome diamond tool is defined by the intersection of naturally occurring (320) and (111) crystal planes.

The ultramicrotome diamond tool of the present invention is fixed in novel relation to a movable material specimen to be cut. The material specimen has a longitudinal axis. The material specimen is advanced in a direction along its longitudinal axis toward the ultramicrotome tool using conventional techniques. The shank has a longitudinal axis and is fixed on a base so that the longitudinal axis of the shank is substantially orthogonal to the longitudinal axis of the material specimen. Thus, the shank is fixed on its base in a novel substantially vertical upright orientation shown in FIGS. 5 and 7 rather than in the conventional canted orientation shown in FIG. 2. Such an upright shank orientation advantageously reduces the deleterious effects of knife blade chatter and is a significant improvement over conventional knife blade assemblies.

The invention can best be understood by referring to the following description and accompanying drawings which illustrate preferred embodiments exemplifying the best mode of carrying out the invention as presently perceived. In the drawings:

FIG. 8 is a perspective view of a portion of a diamond crystal lattice structure showing a (111) and a (100) crystal plane;

FIG. 9 is a transverse cross-sectional view of the diamond crystal structure shown in FIG. 8 taken along line 9—9 showing a cutting edge defined by the intersection of the (111) and (100) crystal planes;

An ultramicrotome diamond tool or knife of the present invention includes a cutting edge defined by the intersection of two substantially naturally occurring planar surfaces of a natural or artificially manufactured cubic crystalline structure such as a diamond. Miller indicies are used to identify each family of crystal planes.

One embodiment of an ultramicrotome diamond tool exploits the angular relationship between naturally occurring (111) and (100) crystal planes, is suitable for use in the materials science art, and is illustrated in FIGS. 3, 4, 5, 8, and 9. A second embodiment of an ultramicrotome diamond tool exploits the angular relationship between naturally occurring (320) and (111) crystal planes, is suitable for use in the biological science art, and is illustrated in FIGS. 6, 7, 10, and 11. It is known that a particular angular relationship may be required for one tool application and a slightly different angular relationship may be required for another tool application. The angular relationships between most pairs of intersecting crystal planes are obtainable in known reference sources. Thus, the use of other pairs or combinations of naturally occurring crystal planes in an ultramicrotome diamond tool is also within the scope of and contemplated by the present invention.

Both embodiments of the novel diamond tool advantageously reduce "chatter" by providing cutting edges that keep their sharpness over a longer period of time than conventional diamond tools. This advantage is obtained because at least one of the planar surfaces used to define the cutting edge of the diamond tool is substantially co-planar with a naturally occurring crystal plane. Further, a blade-holding shank of novel construction is used in each embodiment to better support the diamond blade in relation to a material specimen to be cut to significantly reduce "chatter."

Figure 5:
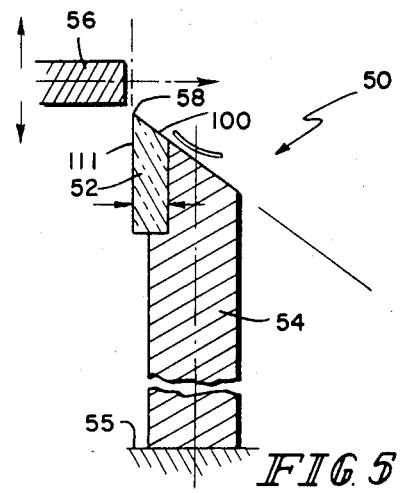
FIG. 5 is a side elevation view of a first embodiment of an ultramicrotome diamond tool according to the present invention showing a cutting edge defined by the intersection of a (111) and a (100) crystal plane in proximity to a movable material specimen to be sliced.

Referring now to FIG. 5, a first embodiment of the present invention includes a first diamond tool 50 having a diamond blade 52 mounted on a shank 54. The shank 54 of the diamond tool is rigidly mounted on a base 55 by conventional means to position the diamond blade 52 in proximity to an advancing material specimen 56 to be cut. The longitudinal axis of the mounted shank is substantially perpendicular to the longitudinal axis of the advancing material specimen. The material specimen 56 is movable relative to the diamond blade 52 in axial and radial directions by any conventional technique such as thermoexpansion of a specimen-carrying metal bar (not shown). Diamond blade 52 includes a cutting edge 58 defined by the intersection of two naturally occurring crystal planes. In particular, a (111) and a (100) plane have been selected since the dihedral angle between those planes is known to be 54.7°. That known angle is very close to the 50° included angle that is the common and standard cutting edge angle in the materials science field. This cutting edge angle is suitable for cutting plastic materials, ceramics, bones, and teeth.

The novel process for making and mounting diamond blade 52 is sequentially illustrated in FIGS. 1, 3, 4, and 5. An octahedrally-shaped diamond 10 is first notched and then cleaved along substantially a (111) crystal plane using conventional techniques to provide a standard triangularly-shaped diamond platelet 14. An octahedral face of any cubic crystalline structure such as diamond, silicon, germanium, and the like is always in the (111) family of crystal planes. A diamond crystal will usually break along a (111) crystal plane when cleaved due to the existence of very weak Carbon-to-Carbon bonds between such planes produced by nitrogen segregation to the (111) crystal plane.

Figures 3, 4:
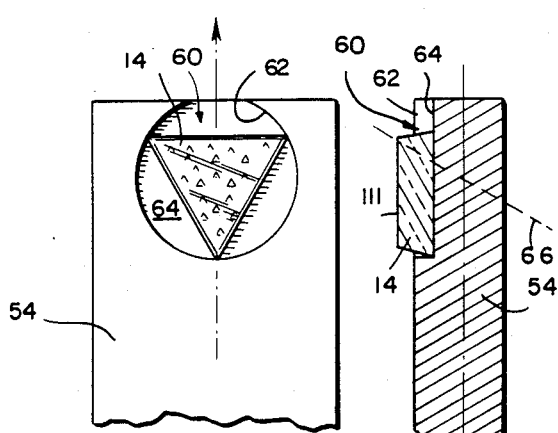
FIG. 3 is a front view of a platelet mounted in a first type of shank according to the present invention.
FIG. 4 is a side elevation view of the platelet and shank shown in FIG. 3 showing the platelet and shank to be severable along a dotted line to provide a first embodiment of an ultramicrotome diamond tool according to the present invention.

The (111) plane is identified by a plurality of little "etch pit" triangular surfaces made visible with a 500x eyepiece microscope by etching platelet 14 in a molten bath of potassium nitrate or other salt. Cleaved platelet 14 is first polished and then placed in the molten salt solution to reveal the edge pit triangles illustrated in FIG. 3. Diamond platelet 14 can be transformed into diamond blade 52 once a plane substantially coplanar with the (111) plane has been obtained and the platelet 14 has been mounted in a milled circular cut-out 60 in one end of shank 54 as shown in FIGS. 3 and 4. Shank 54 can be made of stainless steel, titanium, or the like. The circular cut-out 60 can be formed with an end mill to include a circular side wall 62 and a bottom wall 64. One of the two substantially parallel (111) planes of platelet 14 is placed against bottom wall 64 and the periphery of the diamond platelet 14 is brazed to the metal shank 54 as shown in FIG. 4. The other of the two substantially parallel (111) planes of platelet 14 faces outwardly from cut-out 60 upon completion of the mounting and brazing operations.

Diamond blade 52 is fabricated in a three step process. First, the exposed face 111 is polished in accordance with a novel machining and polishing operation described below. Second, the metal shank 54 and the mounted diamond platelet 14 are severed substantially along a plane represented by broken line 66 in FIG. 4 in accordance with conventional severing techniques. The object of this "roughing" operation is to obtain a plane in close proximity to a naturally occurring (100) crystal plane. As mentioned above the dihedral included angle between (111) and (100) crystal planes is 54.7°. Desirably, the dihedral included angle between the exposed planar face 111 and the severed plane 66 is about three or four degrees greater than the dihedral included angle between the two intersecting naturally occurring crystal planes. This is because the diamond material immediately below the surface of plane 66 will be characterized by unwanted material fatigue. This fatigued material can subsequently be removed to expose a desired diamond crystal plane. Finally, the novel machining and polishing is performed on the severed platelet 14 mounted on metal shank 14 to remove the proper amount of diamond material to expose face 100 of diamond blade 52 as finally shown in FIG. 5. Face 100 is substantially co-planar with a naturally occurring (100) crystal plane and intersects face 111 to define cutting edge 58 of the diamond blade 52. This novel technique removes the fatigued material produced by the "roughing" operation without causing further material fatigue.

Standard diamond machining techniques are usable perform the above-described severing operation on metal shank 54 and diamond platelet 14. For example. use of either a grinding wheel or a charged scaife would be satisfactory. A diamond grinding wheel typically comprises a metal matrix wheel on which diamond grit is bonded by an epoxy. The wheel is similar to a regular grinding wheel; however, it has diamond powders. Further, the wheel is constantly washed in water or solution to keep the metal from sticking and galling to the wheel itself. A charged scaife is a rotating platter. The scaife is charged with a mixture of oil such as whale or olive oil and diamond powder dripped thereon. The scaife has little pores to trap diamond powder therein. This trapped diamond powder is usable to abrasively machine a metal-diamond article such as shank 54 and platelet 14. More metal material than diamond material will be removed using either technigue since the metal is a comparatively softer material. Thus, the metal shank 54 is ground to a lower level than the diamond platelet 14 to expose plane 66. This "elevated" plane 66 is then available for further machining and polishing using the novel technique taught below.

A machining and polishing operation is now performed on the severed platelet 14 mounted on metal shank 54. The machining and polishing operation is also usable to polish the face 111 and is desirably carried out partially in accordance with the teaching of U.S. Pat. No. 4,328,646 and further in accordance with the novel process of the present invention.

The '646 patent discloses how to make a silicone oxide composition that is usable in the novel manner described below to lap or polish the mounted diamond platelet 14 along plane 66. Such a lapping operation removes diamond material by removing selected carbon atoms that are bonded to the diamond crystal on an atom-by-atom basis. This type of lapping operation ultimately furnishes a diamond facet with an atomically smooth surface exhibiting little or no material fatigue below the surface in contrast to the material fatigue caused by the above-described severing or "roughing" operation. Other conventional methods use grinding techniques which remove whole segments of material, create unwanted vibration in the diamond crystal, and significantly damage the crystal structure of the diamond. The lapping operation is continued until a sufficient amount of diamond material has been removed to expose an ultrasmooth second planar face 100 which is substantially coplanar with a (100) crystal plane. Second planar face 100 intersects planar face 111 to define cutting edge 58 of diamond blade 52.

The machining and polishing operation may additionally be carried out in accordance with the teaching of U.S. Pat. No. 4,104,832. The '832 patent discloses how to form a deep coarse-pitched groove in a lapping disc to enable portions of the disc to lap the shoulders of a diamond stylus. The '832 patent discloses a rotatable lapping disc formed to include a helical groove for engaging the tip of a stylus.

Figure 12:
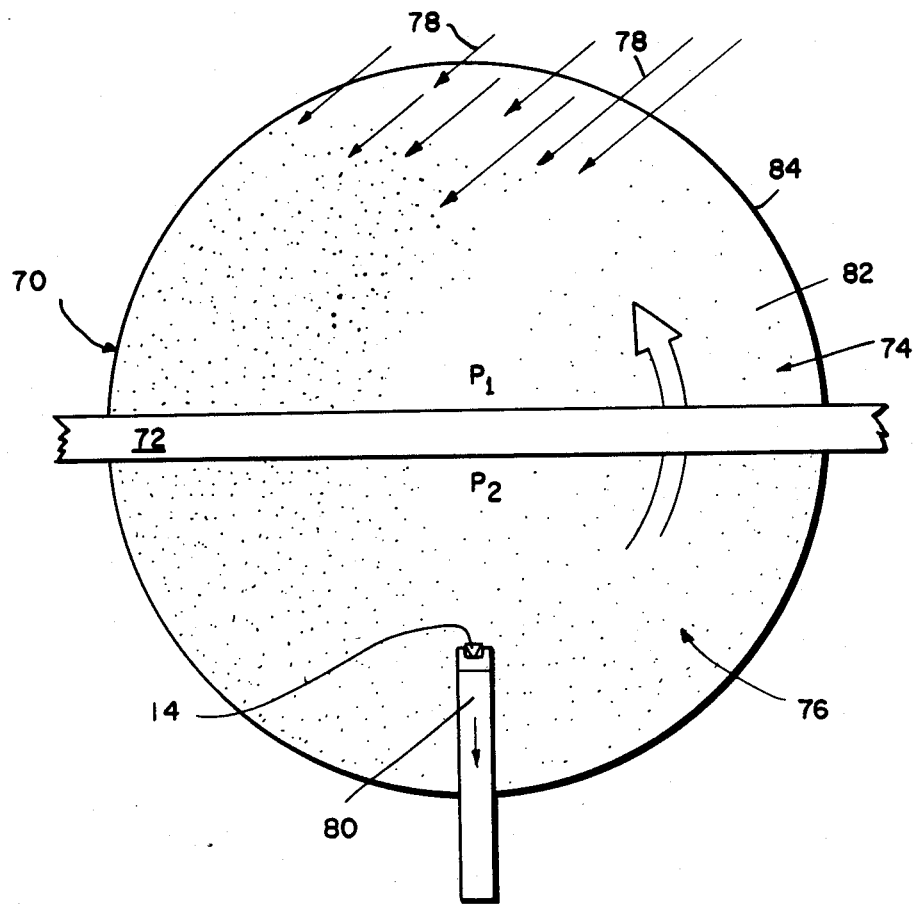
FIG. 12 is a diagramatic top view of a rotatable platter for continuously applying a composition to a mounted diamond to machine and polish the diamond.
Figure 12:
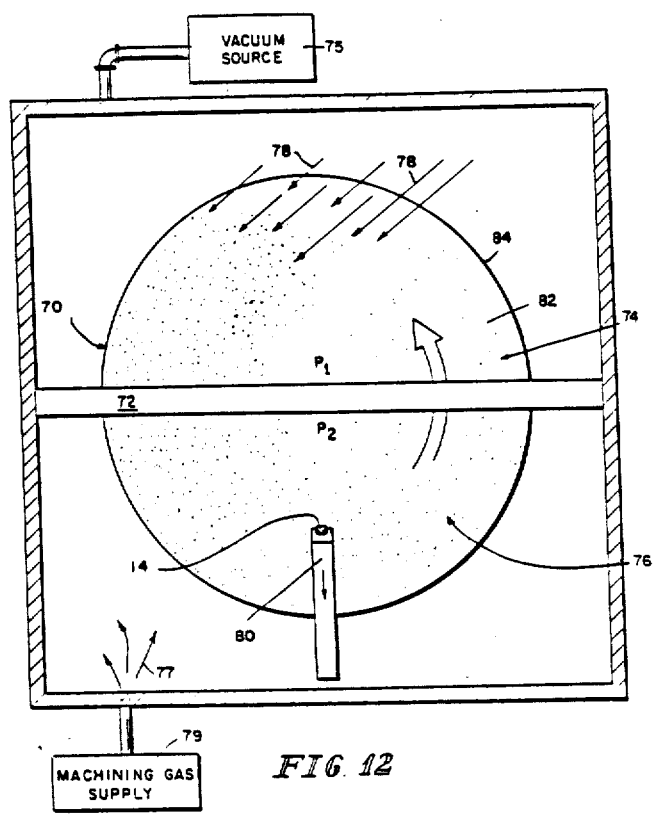

Referring now to FIG. 12, a lapping disc, slap or scaife 70 according to the present invention is shown for continuously machining and polishing the mounted diamond platelet 14 shown in FIG. 4 until a sufficient quantity of carbon atoms have been plucked out of the diamond crystal to expose the planar face 100. The scaife 70 can be made out of a high-silicon, high carbon steel of the type used to polish and hone chromium-piston rings. The scaife 70 can have a flat diamond machining surface as shown in FIG. 12 or it can be formed to include a circular groove similar to the groove shown in the '832 patent for engaging and machining a diamond.

The scaife 70 is rotatable by drive means (not shown) and operable within a bell jar 280. The bell jar 200 surrounding the scaife 70 is divided into two adjacent portions 74, 76 by a pressure isolation bridge 72. A first pressure is caused to exist in a first portion 74, and a selected second pressure greater than the first pressure is caused to exist in a second portion 76. A vacuum is desirably pulled in first portion 74 using vacuum source 75. A "machining" gas 77 such as Oxygen, Argon, $N_2O$, or the like is introduced from machining gas supply 79 into second portion 76.

The above described pressure system uses a differentially pumped seal on the isolation bridge to permit a different pressure to exist in both the first and second portions. This is a common technique employed in vacuum coating large sheets of glass, plastic film, or any other application involving moving parts and requiring a vacuum on one side and atmospheric pressure on the other side.

Scaife 70 is continuously operated in the following manner to machine a diamond such as diamond platelet 14 or any other hard, brittle material. First, a machining compound 78 such as the silicone oxide composition disclosed in the '646 patent is continuously deposited on the rotatable scaife 70 in first portion 74 using plasma deposition techniques. Second, a diamond platelet 14 or other material to be machined is mounted on a mounting fixture 80 in second portion 76 in proximity to the scaife 70. Mounting fixture 80 is movable to selectively cause the platelet 14 housed in second portion 76 to contact the machining compound 78 deposited on the rotatable scaife 70 in first portion 74. Carbon atoms are continuously removed from mounted platelet 14 until such contact with the machining compound 78 is ceased. The platelet 14 is machined in this fashion until the proper planar face 100 corresponding to the (100) plane (for the first embodiment of the diamond tool) is exposed. Of course, the platelet 14 could also be machined to obtain a different included angle should a naturally occurring crystal plane other than the (100) crystal plane be selected. At this point, the plane 66 and the underlying fatigued diamond material has been worn away by machining compound 78. The remaining planar face 100 is substantially coplanar with a naturally occurring (100) crystal plane and is distinguished by its lack of material fatigue.

Scaife 70 is desirably fabricated to include a machining or working surface on its flat top 82 and also on its edge 84. The mounting fixture 80 is movable to cause the crystalline structure mounted thereon to contact either the flat top working surface 82 or the edge working surface 84. As mentioned previously, a groove may be formed in flat top 82 to machine the mounted diamond to a particular edge radius or configuration. The diamond or crystalline structure is "polished" on contact with flat top 82 and is "sliced" on contact with edge 84.

The crystal structure of a diamond that has been machined and polished in the manner described above to obtain a diamond blade 52 having a cutting edge 58 is illustrated in FIGS. 8 and 9. Thus, FIGS. 8 and 9 show a first embodiment of an ultramicrotome diamond tool in which the cutting edge 58 is defined by the intersection of a (111) crystal plane and a (100) crystal plane. A diamond crystal includes a plurality of carbon atoms 90, each carbon atom 90 being covalently bonded (as noted by bonds 92) to four other carbon atoms located at the corners of a regular tetrahedron. Each carbon atom 90 is shown to include four cubic faces 94 and eight octahedral faces 96. As illustrated in FIGS. 8 and 9, a (111) crystal plane is defined by at least two octahedral faces 96 and a (100) crystal plane is defined by at least two cubic faces 94.

Figure 7:
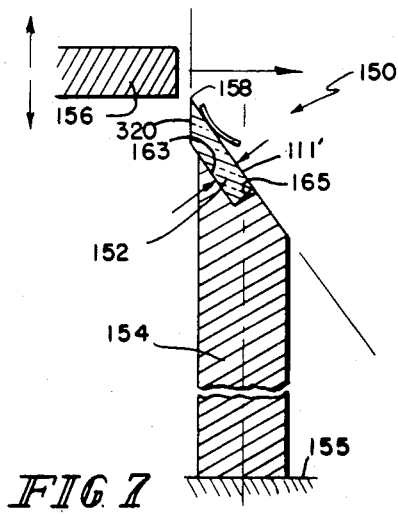
FIG. 7 is a side elevation of a second embodiment of an ultramicrotome diamond tool according to the present invention showing a cutting edge defined by the intersection of a (320) and a (111) plane in proximity to a movable material specimen to be sliced.

Referring now to FIG. 7, a second embodiment of the present invention includes a second diamond tool 150 having a diamond blade 152 mounted on a shank 154. The shank 154 of the diamond tool is rigidly mounted to a base 155 by conventional means to position the diamond blade in proximity to an advancing material specimen 156 to be cut. Diamond blade 152 includes a cutting edge 158 defined by the intersection of two naturally occurring crystal planes. In particular, (320) and (111) planes have been selected since the dihedral angle between those planes is 36.8° and close to the 40° included angle that is the common and standard cutting edge angle in the biological science field. This cutting edge angle is suitable for cutting leathers, kidneys, biological specimens, and plant sections.

Figure 1:
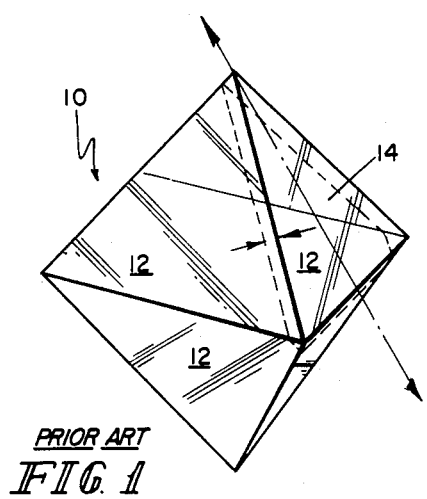
FIG. 1 is a perspective view of an octahedral diamond crystal showing a (111) plane along which the crystal may be cleaved to obtain a triangular platelet.
Figure 2:
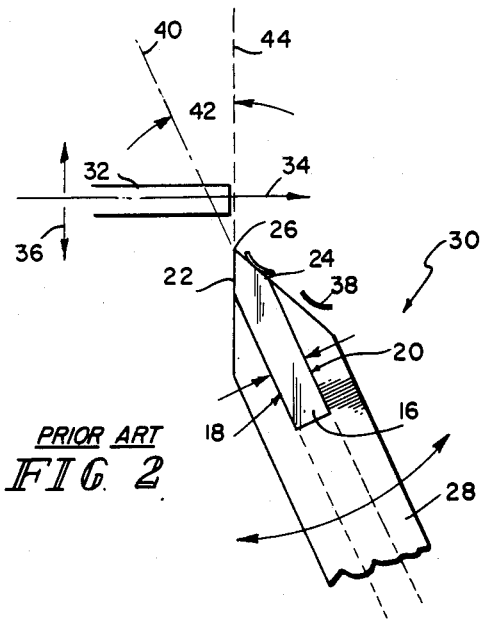
FIG. 2 is a diagramatic side elevation view of a conventional diamond tool or knife having a cutting edge defined by the intersection of two non-naturally occurring crystal planes, the fixed knife being shown in proximity to a movable material specimen to be sliced.
Figure 6:
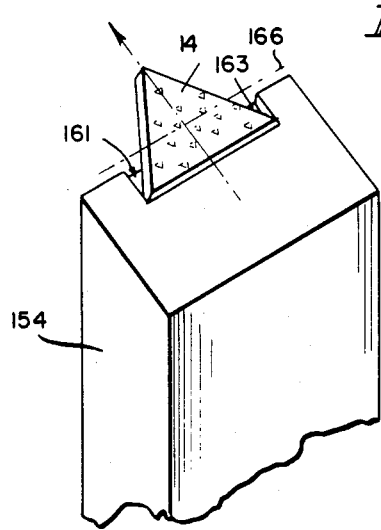
FIG. 6 is a perspective view of a platelet mounted in a second type of shank according to the present invention.

The novel process for making and mounting diamond blade 152 is sequentially illustrated in FIGS. 1, 6, and 7. The process is substantially similar to the process described above in relation to a first embodiment shown in FIG. 5. In this second embodiment, a diamond platelet 14 is mounted in an elongated slot 161 milled in one end of shank 154 as shown in FIGS. 6 and 7. The elongated slot 161 can be formed with an end mill to include a rectangular side wall 163 and a rectangular bottom wall 165. One of the two substantially parallel (111) planes of platelet 14 is placed against side wall 163 and the periphery of diamond platelet 14 is brazed to the metal shank 154 as shown in FIG. 7. The other of the two substantially parallel (111) planes of platelet 14 faces outwardly form side wall 163 upon completion of the mounting and brazing operations.

The metal shank 154 and the mounted diamond platelet 14 are severed substantially along a plane represented by broken line 166. Once again, the object of this severing operation is to obtain a plane in close proximity to a naturally occurring crystal plane. However, in this embodiment a (320) plane is ultimately sought rather than the (100) plane sought in the first embodiment.

The above-described novel machining and polishing operation of the present invention is now performed on the severed platelet 14 mounted on metal shank 154 to remove the proper amount of diamond material to expose face 320 of diamond blade 152 as shown in FIG. 7. Face 320 is substantially coplanar with a naturally occurring (320) crystal plane. Planar face 320 intersects planar face 111' to define cutting edge 158 of diamond blade 152.

Figure 10:
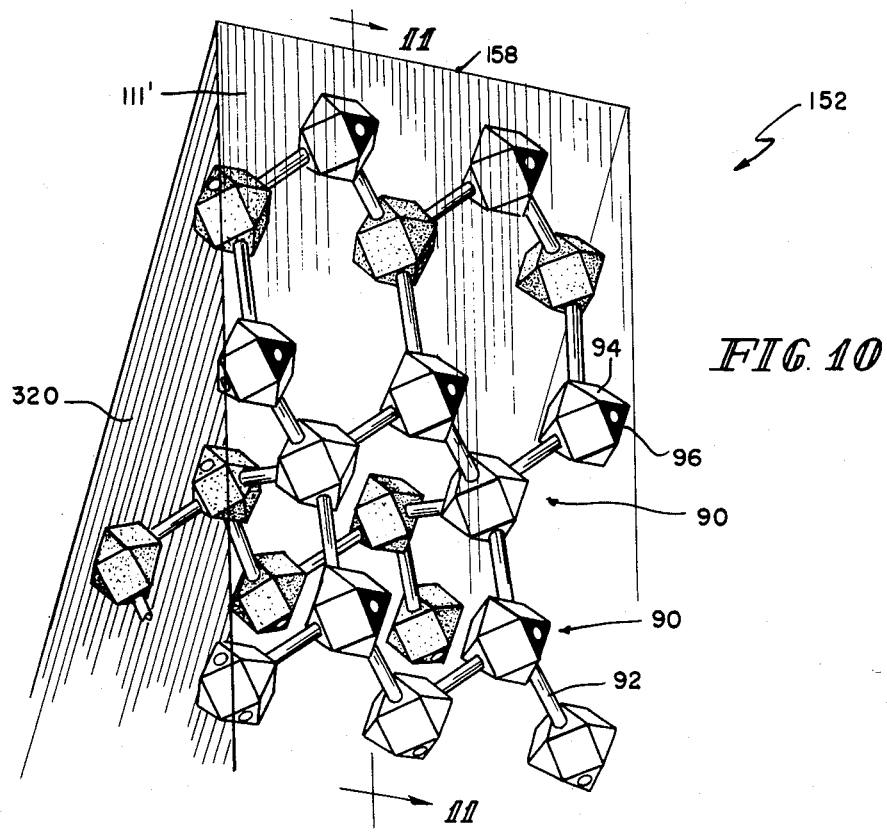
FIG. 10 is a perspective view of a portion of a diamond crystal lattice structure showing a (320) and a (111) crystal plane.
Figure 11:
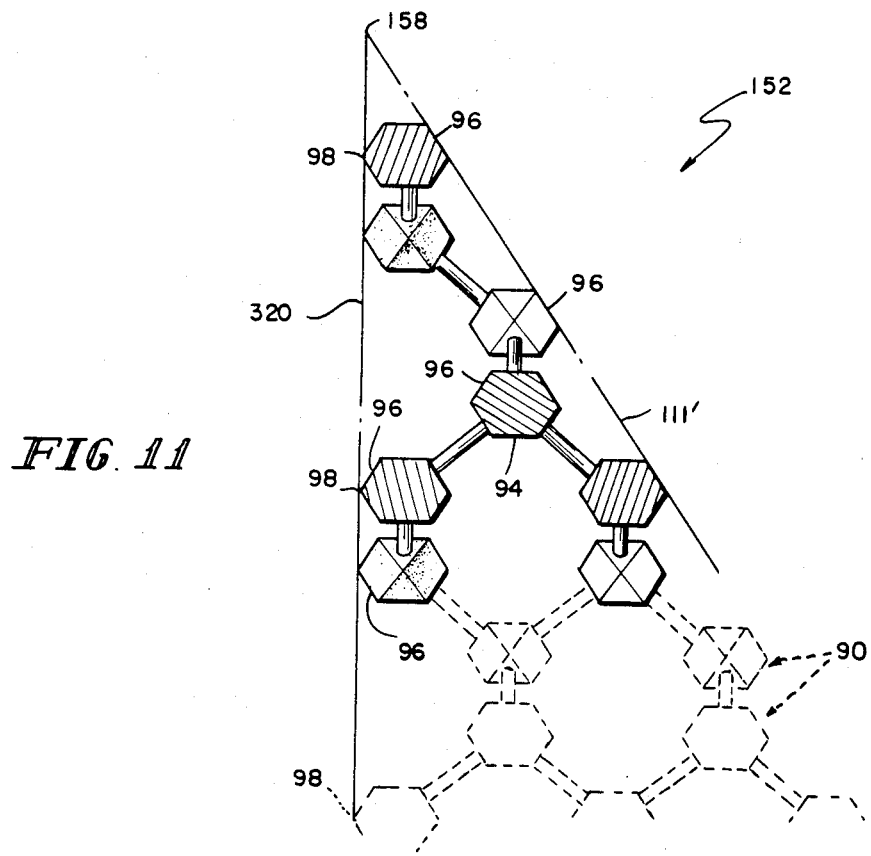
FIG. 11 is a transverse cross-sectional view of the diamond crystal structure shown in FIG. 10 taken along line 11—11 showing a cutting edge defined by the intersection of the (320) and (111) crystal planes.

The crystal structure of a diamond that has been machined and polished to obtain a diamond blade 152 having a cutting edge 158 is illustrated in FIGS. 10 and 11. Thus, FIGS. 10 and 11 show a second embodiment of an ultramicrotome diamond tool in which the cutting edge 158 is defined by the intersection of a (320) crystal plane and a (111) crystal plane. As illustrated in FIGS. 10 and 11, a (111) crystal plane is defined by at least two octahedral faces 96 and a (320) crystal plane is defined by a plane including the common boundary 98 of two contiguous octahedral faces 96.

Although the invention has been described in detail with reference to certain preferred embodiments and specific examples, variations and modifications exist within the scope and spirit of the invention as described and defined in the following claims.

What is claimed:

1. A method of machining a hard and brittle material, the method comprising the steps of
    rotating a platter having surfaces,
    continuously applying a nonabrasive machining composition to one of the platter surfaces in a vacuum during rotation of the platter, and
    during the continuously applying step, positioning the hard and brittle material in proximity to the rotating platter to cause the material to contact the nonabrasive machining composition,
    whereby the nonabrasive machining composition operates on the positioned material to machine and polish the material.

2. The method of claim 1, wherein the nonabrasive machining composition is silicon oxide.

3. The method of claim 1, wherein the nonabrasive machining composition is a mixture of silicon and oxygen containing precursors of $SiO_x$.

4. The method of claim 1, wherein the continuously applying step is accomplished using plasma deposition.

5. The method of claim 1, wherein the hard and brittle material is a diamond and the positioning step comprises the step of removing selected carbon atoms that are bonded to the crystalline structure of diamond on an atom-by-atom basis so that the machined diamond is distinguished by its lack of material fatigue.

6. The method of claim 5, wherein the removing step is repeated until a sufficient amount of diamond material has been removed to expose an ultrasmooth planar face that is substantially coplanar with a naturally occurring crystal plane within the crystalline structure of the diamond.

7. The method of claim 1, wherein the nonabrasive machining composition is continuously applied to the one surface in a first chamber and the material is positioned to contact the nonabrasive machining composition in a second chamber.

8. The method of claim 7, further comprising the steps of
    establishing a first pressure in the first chamber, and
    establishing a second pressure in the second chamber, the second pressure being greater than the first pressure.

9. The method of claim 8, wherein the first pressure is a vacuum.

10. The method of claim 8, further comprising the step of introducing a gas selected from the group consisting essentially of oxygen, argon, and nitrogen oxide into the second chamber.

11. The method of claim 1, further comprising the steps of
    enclosing the platter and a space surrounding the platter within a sealed closure, and
    providing a pressure-isolation bridge to partition the space into the two adjacent chambers, and providing a differentially pumped seal on the pressure-isolation bridge to permit a different pressure to exist in both the first and second chambers.

12. The method of claim 1, further comprising the step of exposing the nonabrasive machining composition and the hard and brittle material to a gas selected from the group consisting essentially of oxygen, argon, and nitrogen oxide during the positioning step.

13. The method of claim 12, further comprising the steps of
    providing a sealed closure having at least one pressure chamber,
    establishing a vacuum in a selected one of the at least one pressure chamber, and
    positioning the rotating platter so that each portion of said surface periodically passes through the selected pressure chamber, the nonabrasive machining composition being applied to each portion of said surface in the selected pressure chamber as said portion passes through the selected pressure chamber.

14. The method of claim 13, wherein the exposing step occurs in a region outside of the selected pressure chamber.

15. A method of machining a hard and brittle material, the method comprising the steps of
    rotating a platter having surface within an enclosure having first and second pressure chambers,
    continuously applying a nonabrasive machining composition to one of the platter surface in the first pressure chamber, and
    during the continuously applying step, positioning the hard and brittle material in the second pressure chamber in proximity to the rotating platter to cause the material to contact the nonabrasive machining composition,
    whereby the nonabrasive machining composition operates on the positioned material to machine and polish the material.

16. The method of claim 15, further comprising the step of exposing the nonabrasive machining compound and the hard and brittle material to a gas selected from the group consisting essentially of oxygen, argon, and nitrogen oxide during the positioning step.

17. The method of claim 15, wherein the continuously applying step includes the step of establishing a vacuum in the first pressure chamber.

18. The method of claim 15, wherein the positioning step includes the step of introducing a gas selected from the group consisting essentially of oxygen, argon, and nitrogen oxide into the second pressure chamber.

19. The method of claim 15, wherein the nonabrasive machining composition is silicon oxide.

20. The method of claim 15, wherein the nonabrasive machining composition is a mixture of silicon and oxygen containing precursors of $SiO_x$.

21. The method of claim 15, wherein the continuously applying step is accomplished using plasma deposition.

22. The method of claim 15, wherein the hard and brittle material is a diamond and the positioning step comprises the step of removing selected carbon atoms that are bonded to the crystalline structure of the diamond on an atom-by-atom basis so that the machined diamond is distinguished by its lack of material fatigue.

23. The method of claim 22, wherein the removing step is repeated until a sufficient amount of diamond material has been removed to expose an ultrasmooth planar face that is substantially coplanar with a naturally occurring crystal plane within the crystalline structure of the diamond.

24. A method of nonabrasively machining a hard and brittle material, the method comprising the steps of
positioning the hard and brittle material in a fixed predetermined position,
providing nonabrasive machining composition,
contacting the positioned hard and brittle material with nonabrasive machining composition without interruption during a machining cycle, and
during the contacting step, exposing the nonabrasive machining composition and the positioned hard and brittle material to a gas selected from the group consisting essentially of oxygen, argon, and nitrogen oxide, and removing selected carbon atoms that are normally chemically bonded to the crystal structure of the hard and brittle material, thereby providing an atomically smooth surface on the material exhibiting little or no subsurface fatigue.

25. The method of claim 24, wherein the nonabrasive machining composition is silicon oxide.

26. The method of claim 24, wherein the nonabrasive machining composition is a mixture of silicon and oxygen containing precursors of $SiO_x$.

27. The method of claim 24, wherein the contacting step continues until a sufficient amount of the positioned hard and brittle material has been removed to expose an ultrasmooth planar surface that is substantially coplanar with a naturally occurring crystal plane within the crystalline structure of the hard and brittle material.

* * * * *

UNITED STATES PATENT AND TRADEMARK OFFICE
CERTIFICATE OF CORRECTION

PATENT NO. : 4,643,161

DATED : February 17, 1987

INVENTOR(S) : George A. Kim

Page 1 of 2

It is certified that error appears in the above-identified patent and that said Letters Patent is hereby corrected as shown below:

Figure 12 should read as shown on the attached sheet.

Signed and Sealed this

Twenty-second Day of November, 1988

*Attest:*

DONALD J. QUIGG

*Attesting Officer*    *Commissioner of Patents and Trademarks*